United States Patent
Watanabe (10) Patent No.: US 8,084,646 B2
(45) Date of Patent: Dec. 27, 2011

(54) PROCESS FOR PRODUCTION OF HYDROXYADAMANTANEAMINE

(75) Inventor: Hideaki Watanabe, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 12/447,795

(22) PCT Filed: Sep. 28, 2007

(86) PCT No.: PCT/JP2007/068962
§ 371 (c)(1),
(2), (4) Date: Apr. 29, 2009

(87) PCT Pub. No.: WO2008/053652
PCT Pub. Date: May 8, 2008

(65) Prior Publication Data
US 2010/0105923 A1     Apr. 29, 2010

(30) Foreign Application Priority Data
Nov. 2, 2006 (JP) ................. 2006-298431

(51) Int. Cl.
*C07C 211/00* (2006.01)
*C07C 211/17* (2006.01)
*C07C 211/19* (2006.01)
*C07C 65/00* (2006.01)

(52) U.S. Cl. ......... 564/336; 564/384; 564/387; 562/474

(58) Field of Classification Search .......... None
See application file for complete search history.

(56) References Cited

FOREIGN PATENT DOCUMENTS

| | | | |
|---|---|---|---|
| EP | 1 953 145 A1 | 11/2006 | |
| EP | 1 894 919 A1 | 3/2008 | |
| EP | 2 006 286 A2 | 12/2008 | |
| JP | 43-3185 A | 2/1968 | |
| SU | 740752 A1 | 6/1980 | |
| WO | WO 95/00146 A1 | 1/1995 | |
| WO | WO 2004/056745 A2 | 7/2004 | |
| WO | WO 2005/016877 A2 | 2/2005 | |
| WO | WO 2005/108368 A1 | 11/2005 | |
| WO | WO 2006/132197 A1 | 12/2006 | |
| WO | WO 2007/051811 A2 | 5/2007 | |
| WO | WO 2007/058346 A1 | 5/2007 | |
| WO | WO 2007/077949 A1 | 7/2007 | |
| WO | WO 2007/114124 A1 | 10/2007 | |

OTHER PUBLICATIONS

Vippagunta et al. "Crystalline Solids" Advanced Drug Delivery Reviews 48 (2001) 3-26.*
Sasaki et al J. Org. Chem. (1982), 47(27), 5250-5255.*
Sasaki et al J. Chem. Soc., Chem. Comm (1979), (11), 506-507.*
International Search Report of PCT/JP2007/068962, dated Nov. 27, 2007.
Lavrova et al. "Some Amino Alcohols of the Adamantane Series and their Derivatives." Zhurnal Organicheskoi Khimii. vol. 12(11), Nov. 1976, pp. 2369-2374. (English Translation Only pp. 2299-2304).
Jaroskova et al. "An expeditious preparation of *E*-2-amino-5-hydroxyadamantane and its *Z*-isomer," Tetrahedron Letters, 47, 2006, pp. 8063-8067.
Klimova et al., Hydroxyaminoadamantanes and their biological activity, Khimiko Farmatsevticheskii Zhurnal, 20(7), 1986, pp. 810-815, English Abstract; see also IDS.

* cited by examiner

*Primary Examiner* — Kamal Saeed
*Assistant Examiner* — Nyeemah A Grazier
(74) *Attorney, Agent, or Firm* — Hamre, Schumann, Mueller & Larson, P.C.

(57) ABSTRACT

Disclosed is a process for producing 1-hydroxy-4-aminoadamantane.

2 Claims, 1 Drawing Sheet

[Fig.1]

PROCESS FOR PRODUCTION OF HYDROXYADAMANTANEAMINE

FIELD OF THE INVENTION

The present invention relates to a process for producing 1-hydroxy-4-aminoadamantane.

BACKGROUND ART

1-Hydroxy-4-aminoadamantane is a compound useful as a raw material for, or an intermediate for synthesizing a medicament and, for example, can be utilized as an intermediate for synthesizing a compound having 11 β-hydroxy steroid dehydrogenase inhibiting activity described in Patent Document 1, Patent Document 2 and Patent Document 3.

Non-Patent Document 1 and Non-Patent Document 2 disclose a process for producing 1-hydroxy-4-aminoadamantane by reacting 2-aminoadamantane with a mixture of nitric acid and sulfuric acid to perform hydroxylation. In the reaction, a ratio of produced diastereomers is advantageous for a syn isomer, and syn isomer:anti isomer is 3:1 to 1:1.

Table 1, Entry 6 in Non-Patent Document 3 discloses that 5-hydroxy-2-adamantanone and benzylamine are reacted in the presence of $H_2$/5% Pt—C, and anti isomer:syn isomer is obtained at 1:1. In addition, Table 2, Entry 8 discloses that 5-hydroxy-2-adamantanone and benzylamine are reacted in the presence of $H_2$/5% Rh—C and Al $(iOPr)_3$, and anti isomer:syn isomer is obtained at 2.7:1. A production ratio of anti isomer/syn isomer in these two experimental examples was measured by $^1$H-NMR, and any compounds were not isolated.

Patent Document 1 discloses a process for producing an anti isomer of 1-hydroxy-4-aminoadamantane by reacting 5-hydroxy-2-adamantanone and L (−)-1-phenyl-ethylamine in the presence of a heterogeneous catalyst (e.g. rhodium supported on carbon), purifying the resulting diastereomers by column chromatography, isolating an anti isomer, and subjecting the isomer to debenzylation.

Patent Document 2 discloses a process for producing an anti isomer by reacting 5-hydroxy-2-adamantanone and ammonia/methanol in the presence of sodium borohydride, amidating the resulting diastereomer mixture, and purifying the resulting amido isomer by column chromatography.

Patent Document 3 discloses a process for producing an anti isomer by subjecting a diastereomer mixture of 1-hydroxy-4-aminoadamantane, and carboxylic acid to amidation, and purifying the resulting amido isomer by column chromatography.

In the processes described in any document, it is necessary to purify the resulting diastereomer mixture by column chromatography, and industrial utilization was difficult.

[Non-Patent Document 1] Zhurnal Organicheskoi Khimii 1976, 12(11), 2369
[Non-Patent Document 2] Khimiko Farmatsevticheskii Zhurnal 1986, 20(7), 810
[Non-Patent Document 3] Tetrahedron Letters 47 (2006) 8063
[Patent Document 1] WO 04/056745
[Patent Document 2] WO 05/108368
[Patent Document 3] WO 05/016877

DISCLOSURE OF INVENTION

Problems to be Solved by the Invention

The present invention provides an effective process for producing 1-hydroxy-4-aminoadamantane useful as a raw material for, or an intermediate for synthesizing a medicament.

Means to Solve the Problems

The present inventor have found that, as an effective process for producing 1-hydroxy-4-aminoadamantane, unlike Patent Document 1, 5-hydroxy-2-adamantanone, and benzylamine represented by the formula (I) are reacted in the presence of a reducing agent, and the resulting diastereomer can be purified by crystallization. In addition, it has found that, by subjecting the resulting anti isomer to debenzylation, an anti isomer of 1-hydroxy-4-aminoadamantane can be produced at a high purity.

The present invention includes:
(1) A process for producing a compound represented by the formula (II):

[Formula 2]

(wherein $R^1$ and $R^2$ are as defined below)
comprising reacting a compound represented by the formula (I):

[Formula 1]

(wherein $R^1$ and $R^2$ are each independently hydrogen, halogen, carboxy, nitro, optionally substituted alkyl, optionally substituted alkoxy, optionally substituted alkylsulfonyl, optionally substituted arylsulfonyl, or optionally substituted sulfamoyl, or $R^1$ and $R^2$, when a binding carbon atom is adjacent, may be taken together with an adjacent carbon atom to form an optionally substituted ring)
and 5-hydroxy-2-adamantanone in the presence of a reducing agent;
(2) The process according to the above (1), comprising reductive amination in which an acid is added;
(3) The process according to the above (2), wherein the acid is an organic acid or an inorganic acid (with the proviso that, an acid composed of a metal compound is excluded);
(4) The process according to any one of the above (1) to (3), wherein the reducing agent used in reductive amination is a hydride reducing agent;

(5) The process according to any one of the above (1) to (3), wherein the reducing agent is a reducing agent selected from the group consisting of sodium triacetoxyhydroborate, sodium borohydride, lithium tetrahydroborate, pyridine borane complex, tetrahydrofuran borane complex, dimethyl sulfite-borane complex, 2-picoline borane complex and sodium;

(6) The process according to any one of the above (3) to (5), wherein the solvent used is a solvent selected from the group consisting of N,N-dimethylformamide, dimethyl sulfoxide, xylene, dichloromethane, chloroform, 1,2-dichloroethane, diethyl ether, dioxane, 1,2-dimethoxyethane, acetonitrile, methanol, ethanol, isopropanol, tert-butanol, toluene, tetrahydrofuran and water;

(7) The process according to the above (6), wherein the solvent used is dichloromethane, methanol or ethanol;

(8) A process for producing a compound represented by the formula (III) comprising separating a compound represented by the formula (III):

[Formula 4]

(III)

(wherein $R^1$ and $R^2$ are as defined in the above (1))
from a compound represented by the formula (II):

[Formula 3]

(II)

(wherein $R^1$ and $R^2$ are as defined in the above (1));

(9) A process for producing a compound represented by the formula (IV):

[Formula 6]

(IV)

comprising deprotecting a compound represented by the formula (III):

[Formula 5]

(III)

(wherein $R^1$ and $R^2$ are as defined in the above (1));

(10) The process for producing a compound represented by the formula (IV):

[Formula 8]

(IV)

according to the above (9), comprising a step of producing a compound represented by the formula (III):

[Formula 7]

(III)

(wherein $R^1$ and $R^2$ are as defined in the above (1))
by the process according to the above (8);

(11) The process for producing a compound (IV):

[Formula 10]

(IV)

according to the above (10), comprising a step of producing a compound represented by the formula (II):

[Formula 9]

(wherein $R^1$ and $R^2$ are as defined in the above (1))
by the process according to any one of the above (1) to (7);

(12) A compound represented by the formula (II):

[Formula 11]

(wherein $R^1$ and $R^2$ are as defined in the above (1))
or a salt thereof or a solvate thereof;

(13) A compound represented by the formula (II):

[Formula 12]

(wherein $R^1$ and $R^2$ are each independently hydrogen, halogen, carboxy, nitro, optionally substituted alkyl, optionally substituted alkoxy, optionally substituted alkylsulfonyl, optionally substituted arylsulfonyl, or optionally substituted sulfamoyl, or $R^1$ and $R^2$, when a binding carbon atom is adjacent, may be taken together with an adjacent carbon atom to form an optionally substituted ring) (with the proviso that, the case where $R^1$ and $R^2$ are hydrogen at the same time is excluded),
or a salt thereof, or a solvate thereof;

(14) A compound represented by the formula (III):

[Formula 13]

(wherein $R^1$ and $R^2$ are as defined in the above (1))
or a salt thereof, or a solvate thereof;

(15) A compound represented by the formula (III):

[Formula 14]

(wherein $R^1$ and $R^2$ are each independently hydrogen, halogen, carboxy, nitro, optionally substituted alkyl, optionally substituted alkoxy, optionally substituted alkylsulfonyl, optionally substituted arylsulfonyl, or optionally substituted sulfamoyl, or $R^1$ and $R^2$, when a binding carbon atom is adjacent, may be taken together with an adjacent carbon atom to form an optionally substituted ring) (with the proviso that, the case where $R^1$ and $R^2$ are hydrogen at the same time is excluded),
or a salt thereof, or a solvate thereof;

(16) A process for producing a compound represented by the formula (VI):

[Formula 15]

comprising obtaining a compound (IV) by the process according to any one of the above (9) to (11), and reacting the resulting (IV) with a compound represented by the formula (V): A-$R^3$—$R^4$—$R^5$—X (wherein A is an optionally substituted cyclic hydrocarbon group or an optionally substituted heterocyclic group, $R^3$ is a single bond, —C(=O)—, —O— or —NR$^6$—, $R^4$ is a single bond or optionally substituted alkylene, $R^5$ is a single bond or —C(=O)—, X is a hydroxy group, halogen, or a leaving group derived from a hydroxy group, and $R^6$ is a hydrogen or optionally substituted alkyl);

(17) A crystal of compound represented by the formula (III):

[Formula 16]

(wherein $R^1$ and $R^2$ are as defined in the above (1))
or a salt thereof or a solvate thereof;
(18) The crystal according to the above (17), wherein $R^1$ and $R^2$ are each independently hydrogen, halogen, optionally substituted alkyl or optionally substituted alkoxy; and
(19) The crystal according to the above (17) or (18), wherein $R^1$ and $R^2$ are hydrogen, and a diffraction angle 2θ of a main peak of powder X ray diffraction is 9.9, 14.8, 16.0, 17.2, 17.5, and 19.8 degree.

Effect of the Invention

As apparent from test results described later, the compound (IV) of the present invention is a compound useful as a raw material for, or an intermediate for synthesizing a medicament. In addition, the novel process for producing the compound (IV) can be utilized for industrial production as a high yield and safe process.

BEST MODE FOR CARRYING OUT THE INVENTION

In the present specification, "halogen" includes fluorine, chlorine, bromine or iodine. Particularly, fluorine, chlorine and bromine are preferable.

"Alkyl" includes a straight or branched alkyl group having 1 to 10 carbon atom(s), and example includes methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl, n-nonyl, n-decyl or the like. Preferable is alkyl having 1 to 6 or 1 to 4 carbon atom(s), and example includes methyl, ethyl, n-propyl, isopropyl, n-butyl, isobutyl, sec-butyl, tert-butyl, n-pentyl, isopentyl, neopentyl, n-hexyl, or isohexyl.

"Cycloalkyl" includes a cyclic saturated hydrocarbon group having 3 to 15 carbon atoms, and example includes cyclopropyl, cyclobutyl, cyclopentyl, cyclohexyl, cycloheptyl, cyclooctyl, a bridged cyclic hydrocarbon group, a Spiro hydrocarbon group or the like. Preferable example includes cyclopropyl, cyclobutyl, cyclopentyl, cyclohexyl or a bridged cyclic hydrocarbon group.

"Bridged cyclic hydrocarbon group" includes a group derived by removing one hydrogen atom from an aliphatic cycle having 5 to 8 carbon atoms which consists of two or more rings share two or more atoms. Specifically, example includes bicyclo[2.1.0]pentyl, bicyclo[2.2.1]heptyl, bicyclo[2.2.2]octyl, bicyclo[3.2.1]octyl, tricyclo[2.2.1.0]heptyl or the like.

"Spiro hydrocarbon group" includes a group derived by removing one hydrogen from a cycle which consists of two hydrocarbon rings that share one carbon atom. Specifically, example includes spiro[3.4]octyl or the like.

"Halogenated alkyl" includes alkyl substituted with one or more halogen atoms. The alkyl part and the halogen part are as described above.

"Alkenyl" includes straight or branched alkenyl having 2 to 8 carbon atoms and one or more double bonds in the above "alkyl", and example includes vinyl, 1-propenyl, 2-propenyl, 1-butenyl, 2-butenyl, 3-butenyl, 1,3-butadienyl, 3-methyl-2-butenyl or the like.

"Cycloalkenyl" includes a cyclic unsaturated aliphatic hydrocarbon group having 3 to 7 carbon atoms, and example includes cyclopropenyl, cyclobutenyl, cyclopentenyl, cyclohexenyl or cycloheptenyl, preferably cyclopropenyl, cyclobutenyl, cyclopentenyl or cyclohexenyl. Cycloalkenyl also includes a bridged cyclic hydrocarbon group and a Spiro hydrocarbon group having an unsaturated bond in a ring.

"Alkynyl" includes straight or branched alkynyl having 2 to 8 carbon atoms and one or more triple bonds in the above "alkyl", and example includes ethynyl, propynyl, butynyl or the like.

"Aryl" includes a monocyclic aromatic hydrocarbon group (e.g.: phenyl) or a polycyclic aromatic hydrocarbon group (e.g.: 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl and the like). Preferable example includes phenyl or naphthyl (1-naphthyl, 2-naphthyl).

"Heteroaryl" includes a monocyclic aromatic heterocyclic group or a fused aromatic heterocyclic group. The monocyclic aromatic heterocyclic group means a group which is derived from a 5- to 8-membered aromatic ring optionally containing 1 to 4 of an oxygen atom, a sulfur atom and/or a nitrogen atom in the ring, and may have a bond at a substitutable arbitrary position. The fused aromatic heterocyclic group includes a group in which a 5- to 8-membered aromatic ring optionally containing 1 to 4 of an oxygen atom, a sulfur atom, and/or a nitrogen atom in a ring is fused with 1 to 4 of 5- to 8-membered aromatic carbocycle(s) or other 5- to 8-membered aromatic heterocycle(s), and which may have a bond at a substitutable arbitrary position.

Example of the "heteroaryl" includes furyl (e.g.: 2-furyl, 3-furyl), thienyl (e.g.: 2-thienyl, 3-thienyl), pyrrolyl (e.g.: 1-pyrrolyl, 2-pyrrolyl, 3-pyrrolyl), imidazolyl (e.g.: 1-imidazolyl, 2-imidazolyl, 4-imidazolyl), pyrazolyl (e.g.: 1-pyrazolyl, 3-pyrazolyl, 4-pyrazolyl), triazolyl (e.g.: 1,2,4-triazol-1-yl, 1,2,4-triazol-3-yl, 1,2,4-triazol-4-yl), tetrazolyl (e.g.: 1-tetrazolyl, 2-tetrazolyl, 5-tetrazolyl), oxazolyl (e.g.: 2-oxazolyl, 4-oxazolyl, 5-oxazolyl), isoxazolyl (e.g.: 3-isoxazolyl, 4-isoxazolyl, 5-isoxazolyl), thiazolyl (e.g.: 2-thiazolyl, 4-thiazolyl, 5-thiazolyl), thiadiazolyl, isothiazolyl (e.g.: 3-isothiazolyl, 4-isothiazolyl, 5-isothiazolyl), pyridyl (e.g.: 2-pyridyl, 3-pyridyl, 4-pyridyl), pyridazinyl (e.g.: 3-pyridazinyl, 4-pyridazinyl), pyrimidinyl (e.g.: 2-pyrimidinyl, 4-pyrimidinyl, 5-pyrimidinyl), furazanyl (e.g.: 3-furazanyl), pyrazinyl (e.g.: 2-pyrazinyl), oxadiazolyl (e.g.: 1,3,4-oxadiazol-2-yl,), benzofuryl (e.g.: 2-benzo[b]furyl, 3-benzo[b]furyl, 4-benzo[b]furyl, 5-benzo[b]furyl, 6-benzo[b]furyl, 7-benzo[b]fury), benzothienyl (e.g.: 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyl (e.g.: 1-benzimidazolyl, 2-benzimidazolyl, 4-benzimidazolyl, 5-benzimidazolyl), dibenzofuryl, benzoxazolyl, quinoxalyl (e.g.: 2-quinoxalinyl, 5-quinoxalinyl, 6-quinoxalinyl), cinnolinyl (e.g.: 3-cinnolinyl, 4-cinnolinyl, 5-cinnolinyl, 6-cinnolinyl, 7-cinnolinyl, 8-cinnolinyl), quinazolyl (e.g.: 2-quinazolinyl, 4-quinazolinyl, 5-quinazolinyl, 6-quinazolinyl, 7-quinazolinyl, 8-quinazolinyl), quinolyl (e.g. 2-quinolyl, 3-quinolyl, 4-quinolyl, 5-quinolyl, 6-quinolyl, 7-quinolyl, 8-quinolyl), phthalazinyl (e.g.: 1-phthalazinyl, 5-phthalazinyl, 6-phthalazinyl), isoquinolyl (e.g.: 1-isoquinolyl, 3-isoquinolyl, 4-isoquinolyl, 5-isoquinolyl, 6-isoquinolyl, 7-isoquinolyl, 8-isoquinolyl), puryl, pteridinyl (e.g.: 2-pteridinyl, 4-pteridinyl, 6-pteridinyl, 7-pteridinyl), carbazolyl, phenanthridinyl, acridinyl (e.g.: 1-acridinyl, 2-acridinyl, 3-acridinyl, 4-acridinyl, 9-acridinyl), indolyl (e.g.: 1-indolyl, 2-indolyl, 3-indolyl, 4-indolyl, 5-indolyl, 6-indolyl, 7-indolyl), isoindolyl, phenazinyl (e.g.: 1-phenazinyl, 2-phenazinyl), phenothiazinyl (e.g.: 1-phenothiazinyl, 2-phenothiazinyl, 3-phenothiazinyl, 4-phenothiazinyl) or the like.

"Heterocycle" includes a non-aromatic heterocyclic group optionally containing 1 to 4 of an oxygen atom, a sulfur atom, and/or a nitrogen atom in a ring, and may have a bond at a substitutable arbitrary position. In addition, such a non-aromatic heterocyclic group may be further bridged with an alkyl chain having 1 to 4 carbon atom(s), or may be fused with cycloalkane (5- to 6-membered ring is preferable) or a benzene ring. The heterocycle may be saturated or unsaturated as far as it is non-aromatic. Preferable is a 5- to 8-membered ring. Example includes 1-pyrrolinyl, 2-pyrrolinyl, 3-pyrrolinyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidinyl, 3-piperidinyl, 4-piperidinyl, 1-piperazinyl, 2-piperazinyl, 2-morpholinyl, 3-morpholinyl, morpholino, tetrahydropyranyl or the like.

"Cyclic hydrocarbon group" includes the above "cycloalkyl", "cycloalkenyl", or "aryl".

"Heterocyclic group" includes the above "heteroaryl or heterocycle".

The alkyl part of "alkoxy", "alkoxycarbonyl", "alkylsulfonyl", "alkylcarbonyl" and "alkylthio" means the above "alkyl".

The cycloalkyl part of "cycloalkylsulfonyl", "cycloalkyloxycarbonyl" and "cycloalkylcarbonyl" means the above "cycloalkyl".

The aryl part of "aryloxy", "aryloxycarbonyl", "arylsulfonyl", "arylcarbonyl" and "arylthio" means the above "aryl".

The heteroaryl part of "heteroarylcarbonyl", "heteroarylsulfonyl" and "heteroaryloxycarbonyl" means the above "heteroaryl".

The heterocycle part of "heterocyclecarbonyl", "heterocyclesulfonyl" and "heterocycleoxycarbonyl" means the above "heterocycle."

The alkoxy part and the halogen part of "halogenated alkoxy" are as described above.

"Acyl" includes formyl, optionally substituted alkylcarbonyl, optionally substituted alkenylcarbonyl, optionally substituted cycloalkylcarbonyl, optionally substituted cycloalkenylcarbonyl, optionally substituted arylcarbonyl, optionally substituted heteroarylcarbonyl, or optionally substituted heterocyclecarbonyl.

"Aralkyl" means the above "alkyl" substituted with 1 to 3 of the above "aryl".

The aralkyl part of "aralkylcarbonyl" is as described above.

"Alkylene" includes a divalent group comprising 1 to 6 methylene(s) and, specifically, example includes methylene, ethylene, trimethylene, tetramethylene, pentamethylene, hexamethylene or the like.

$R^1$ and $R^2$, when a binding carbon atom is adjacent, may be taken together with an adjacent carbon atom to form a ring. The ring means a 5- to 7-membered (preferably, 5-membered or 6-membered) saturated or unsaturated ring optionally containing 1 to 3 hetero atom(s). For example, as a cyclic group which is formed by $R^1$ and $R^2$ with a benzene ring to which they bind, the following groups are exemplified.

[Formual 17]

Example of the "leaving group derived from hydroxy group" includes —OMs, —OTs, —OTf, —ONs or the like. Wherein, "Ms" represents a methanesulfonyl group, "Ts" represents a para-toluenesulfonyl group, "Tf" represents a trifluoromethanesulfonyl group, and "Ns" represents an orthonitrobenzenesulfonyl group.

"Optionally substituted alkyl", "optionally substituted alkoxy", "optionally substituted alkylsulfonyl", "optionally substituted arylsulfonyl", "optionally substituted sulfamoyl", "optionally substituted ring formed by $R^1$ and $R^2$ together with an adjacent carbon atom", "optionally substituted cyclic hydrocarbon group", "optionally substituted heterocyclic group", and "optionally substituted alkylene" may be substituted with 1 to 4 substituent(s) selected from a group consisting of, for example, hydroxy, carboxy, halogen, halogenated alkyl (e.g. $CF_3$, $CH_2CF_3$, $CH_2CCl_3$), alkyl (e.g.: methyl, ethyl, isopropyl, tert-butyl), alkenyl (e.g.: vinyl), alkynyl (e.g.: ethynyl), cycloalkyl (e.g.: cyclopropyl), cycloalkenyl (e.g.: cyclopropenyl), alkoxy (e.g.: methoxy, ethoxy, propoxy, butoxy), halogenated alkoxy (e.g.: $OCF_3$), alkenyloxy (e.g.: vinyloxy, allyloxy), aryloxy (e.g.: phenoxy), alkoxycarbonyl (e.g.: methoxycarbonyl, ethoxycarbonyl, tert-butoxycarbonyl), nitro, nitroso, optionally substituted amino (e.g.: alkylamino (e.g.: methylamino, ethylamino, dimethylamino), acylamino (e.g.: acetylamino, benzoylamino), aralkylamino (e.g.: benzylamino, tritylamino), hydroxyamino, alkoxycarbonylamino, alkylsulfonylamino, carbamoylamino, heterocyclecarbonylamino, arylsulfonylamino), azido, aryl (e.g.: phenyl), aralkyl (e.g.: benzyl), cyano, isocyano, isocyanate, thiocyanate, isothiocyanate, mercapto, alkylthio (e.g.: methylthio), alkylsulfonyl (e.g.: methanesulfonyl, ethanesulfonyl), optionally substituted carbamoyl (e.g.: alkylcarbamoyl (e.g.: methylcarbamoyl, ethylcarbamoyl, dimethylcarbamoyl), alkylsulfonylcarbamoyl), sulfamoyl, acyl (e.g.: formyl, acetyl), formyloxy, haloformyl, oxalo, thioformyl, thiocarboxy, dithiocarboxy, thiocarbamoyl, sulfino, sulfo, sulfonyl, sulfinyl, sulfoamino, hydrazino, azido, ureido, amidino, guanidino, phthalimido, oxo, cycloalkyl, cycloalkenyl, aryl, heteroaryl, heterocycle, alkylene, optionally substituted alkylenedioxy (—O—CH$_2$—O—, —O—CH$_2$—CH$_2$—O—, —O—CH$_2$—CH$_2$—CH$_2$—O— etc.), heteroaryloxy, heterocycleoxy, alkoxycarbonyl, aryloxycarbonyl, heteroaryloxycarbonyl, heterocycleoxycarbonyl, alkylcarbonyloxy, arylcarbonyloxy, heteroarylcarbonyloxy, heterocyclecarbonyloxy, alkylcarbonyl, arylcarbonyl, heteroarylcarbonyl, heterocyclecarbonyl, alkylthio, arylthio, heteroarylthio, heterocyclethio, alkylsulfonyl, arylsulfonyl, heteroarylsulfonyl, heterocyclesulfonyl, thiocarbamoyl, sulfamoyl and the like.

"Optionally substituted cycloalkyl", "optionally substituted cycloalkenyl", "optionally substituted aryl", "optionally substituted heteroaryl", "optionally substituted heterocycle", "optionally substituted alkylene", "optionally substituted alkylenedioxy", "optionally substituted heteroaryloxy", "optionally substituted heterocycleoxy", "optionally substituted alkoxycarbonyl", "optionally substituted aryloxycarbonyl", "optionally substituted heteroaryloxycarbonyl", "optionally substituted heterocycleoxycarbonyl", "optionally substituted alkylcarbonyloxy", "optionally substituted arylcarbonyloxy", "optionally substituted heteroarylcarbonyloxy", "optionally substituted heterocyclecarbonyloxy", "optionally substituted alkylcarbonyl", "optionally substituted arylcarbonyl", "optionally substituted heteroarylcarbonyl", "optionally substituted heterocyclecarbonyl", "optionally substituted alkylthio", "optionally substituted arylthio", "optionally substituted heteroarylthio", "optionally substituted heterocyclethio", "optionally substituted alkylsulfonyl", "optionally substituted arylsulfonyl", "optionally substituted heteroarylsulfonyl", and "optionally substituted heterocyclesulfonyl" may be substituted with 1 to 4 substituent(s) selected from a group consisting of, for example, hydroxy, carboxy, halogen, halogenated alkyl (e.g.: CF$_3$, CH$_2$CF$_3$, CH$_2$CCl$_3$), alkyl (e.g.: methyl, ethyl, isopropyl, tert-butyl), alkenyl (e.g.: vinyl), alkynyl (e.g.: ethynyl), cycloalkyl (e.g.: cyclopropyl), cycloalkenyl (e.g.: cyclopropenyl), alkoxy (e.g.: methoxy, ethoxy, propoxy, butoxy), halogenated alkoxy (e.g.: OCF$_3$), alkenyloxy (e.g.: vinyloxy, allyloxy), aryloxy (e.g.: phenoxy), alkoxycarbonyl (e.g.: methoxycarbonyl, ethoxycarbonyl, tert-butoxycarbonyl), nitro, nitroso, optionally substituted amino (e.g.: alkylamino (e.g.: methylamino, ethylamino, dimethylamino), acylamino (e.g.: acetylamino, benzoylamino), aralkylamino (e.g.: benzylamino, tritylamino), hydroxyamino, alkoxycarbonylamino, alkylsulfonylamino, carbamolylamino, heterocyclecarbonylamino, arylsulfonylamino), azido, aryl (e.g.: phenyl), aralkyl (e.g.: benzyl), cyano, isocyano, isocyanate, thiocyanate, isothiocyanate, mercapto, alkylthio (e.g.: methylthio), alkylsulfonyl (e.g.: methanesulfonyl, ethanesulfonyl), optionally substituted carbamoyl (e.g.: alkylcarbamoyl (e.g.: methylcarbamoyl, ethylcarbamoyl, dimethylcarbamoyl), alkylsulfonylcarbamoyl), sulfamoyl, acyl (e.g.: formyl, acetyl), formyloxy, haloformyl, oxalo, thioformyl, thiocarboxy, dithiocarboxy, thiocarbamoyl, sulfino, sulfo, sulfonyl, sulfinyl, sulfoamino, hydrazino, azido, ureido, amidino, guanidino, phthalimido, oxo, cycloalkyl, cycloalkenyl, aryl, heteroaryl, heterocycle, alkylene, alkylenedioxy (—O—CH$_2$—O—, —O—CH$_2$—CH$_2$—O—, —O—CH$_2$—CH$_2$—CH$_2$—O— etc.), heteroaryloxy, heterocycleoxy, alkoxycarbonyl, aryloxycarbonyl, heteroaryloxycarbonyl, heterocycleoxycarbonyl, alkylcarbonyloxy, arylcarbonyloxy, heteroarylcarbonyloxy, heterocyclecarbonyloxy, alkylcarbonyl, arylcarbonyl, heteroarylcarbonyl, heterocyclecarbonyl, alkylthio, arylthio, heteroarylthio, heterocyclethio, alkylsulfonyl, arylsulfonyl, heteroarylsulfonyl, heterocyclesulfonyl and the like.

Example of a substituent of "optionally substituted amino", "optionally substituted carbamoyl", "optionally substituted thiocarbamoyl, and "optionally substituted sulfamoyl" includes alkyl, cycloalkyl, alkenyl, cycloalkenyl, aryl, heteroaryl, alkylcarbonyl, arylcarbonyl, heteroarylcarbonyl, heterocyclecarbonyl, alkoxycarbonyl, aryloxycarbonyl, heteroaryloxycarbonyl, heterocycleoxycarbonyl, sulfamoyl, alkylsulfonyl, carbamoyl, cycloalkylsulfonyl, arylsulfonyl, heteroarylsulfonyl, heterocyclesulfonyl, acyl, hydroxy, sulfonyl, sulfinyl, amino or the like.

Among the present compound, as the compound represented by the formula (I), the followings are preferable.

[Formula 18]

-continued

[Formula 19]

A in the formula (V) and the formula (VI) is preferably an optionally substituted heterocyclic group. Further preferably, example includes optionally substituted heteroaryl, or optionally substituted heterocycle. More preferably, example includes furan, thiophene, pyrrole, pyrazole, triazole, oxazole, thiazole, isothiazole, pyridine, morpholine, piperidine, piperazine, pyrrolidine, tetrahydrothiophene, benzoxazine, benzofuran, or pyrrolopyridine. Particularly, isoxazole and pyrazole are preferable, but not limited thereto. In addition as A, an optionally substituted cyclic hydrocarbon group is exemplified. Preferable is phenyl.

Example of a substituent includes —$OR^7$, —$SR^7$, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, a group represented by the formula: —CH=CH—C($R^aR^b$)—$R^c$—$R^d$, a group represented by the formula: —($CR^eR^f$)$_m$—C($R^aR^b$)—$R^c$—$R^d$ or the like.

$R^a$ and $R^b$ are each independently hydrogen, optionally substituted alkyl or halogen, or $R^a$ and $R^b$ may be taken together with an adjacent carbon atom to which they are attached to form an optionally substituted ring, $R^c$ is —$(CH_2)_n$— (wherein n is an integer of 0 to 3), $R^d$ is hydrogen, halogen, hydroxy, carboxy, cyano, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, a group represented by the formula: —C(=O)—$NR^gR^h$ or a group represented by the formula: —$NR^iR^j$, $R^e$ and $R^f$ are each independently hydrogen, halogen or optionally substituted alkyl, $R^g$ and $R^h$ are each independently hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted alkylsulfonyl, optionally substituted cycloalkylsulfonyl, optionally substituted arylsulfonyl, optionally substituted heteroarylsulfonyl, optionally substituted heterocyclesulfonyl, optionally substituted alkoxy, optionally substituted carbamoyl, or $R^g$ and $R^h$ may be taken together with an adjacent nitrogen atom to which they are attached to form an optionally substituted ring, $R^i$ and $R^j$ are each independently hydrogen, carboxy, hydroxy, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted acyl, optionally substituted carbamoyl, optionally substituted thiocarbamoyl, optionally substituted alkylsulfonyl, optionally substituted cycloalkylsulfonyl, optionally substituted arylsulfonyl, optionally substituted heteroarylsulfonyl, optionally substituted heterocyclesulfonyl, optionally substituted alkoxycarbonyl, optionally substituted cycloalkyloxycarbonyl, optionally substituted aryloxycarbonyl, optionally substituted heteroaryloxycarbonyl, optionally substituted heterocycleoxycarbonyl, optionally substituted alkylcarbonyl, optionally substituted cycloalkylcarbonyl, optionally substituted arylcarbonyl, optionally substituted heteroarylcarbonyl, optionally substituted heterocyclecarbonyl, or optionally substituted sulfamoyl, or $R^i$ and $R^j$ may be taken together with an adjacent nitrogen atom to which they are attached to form an optionally substituted ring, $R^7$ is optionally substituted alkyl, optionally substituted alkenyl, optionally substituted cycloalkyl, optionally substituted aryl, optionally substituted heteroaryl or optionally substituted heterocycle, and m is an integer of 1 to 3.

$R^1$ is preferably a single bond.

$R^2$ is preferably a single bond.

$R^3$ is preferably —C(=O)—.

X is preferably a hydroxy group.

Details of compounds represented by the formula (V) and the formula (VI) and processes for producing them are collectively described in International Publication WO 2006/132197, International Publication WO 2007/058346, PCT/JP2007/056538, and Japanese Patent Application No. 2007-132259.

As shown below, among the present compound, the compound represented by the formula (II) is equal to compounds represented by the formula (II') and the formula (II"), the compound represented by the formula (III) is equal to compounds represented by the formula (III') and the formula (III"), and the compound represented by the formula (IV) is equal to compounds represented by the formula (IV') and the formula (IV").

[Formula 20]

(II)

(II')

(II")

(III)

(III')

(III")

(IV)

(IV')

(IV")

In addition, among the present compound, the compound represented by the formula (II") means a mixture of the compound represented by the formula (III) and the compound represented by the formula (III'").

[Formula 21]

"Organic acid" is a generic name of organic compounds exhibiting acidity, and example includes formic acid, acetic acid, benzoic acid, benzenesulfonic acid, citric acid, paratoluenesulfonic acid, methanesulfonic acid, trifluoroacetic acid or the like.

"Inorganic acid" is a generic name of inorganic compounds exhibiting acidity, and example includes hydrochloric acid, sulfuric acid, nitric acid, phosphoric acid or the like.

"Acid composed of metal compound" means a compound containing a metal element among acids which can accept an electron pair upon binding with a base, and example includes Al (i-OPr)$_3$, AlCl$_3$, BF$_3$, TiCl$_4$, FeCl$_3$, ZnCl$_2$, SnCl$_4$ or the like.

"Hydride reducing agent" means a reagent which can donate hydrogen as a nucleophilic agent. Example includes sodium triacetoxyhydroborate, sodium borohydride, lithium tetrahydroborate, pyridine borane complex, tetrahydrofuran borane complex, 2-picoline borane complex, dimethyl sulfide-borane complex, sodium cyanoborohydride, lithium triethylborohydride, lithium aluminum hydride, Red-Al [sodium bis(2-methoxyethoxy)aluminum hydride], L-Selectride [lithium tri(sec-butyl)borohydride], K-Selectride [potassium tri(sec-butyl)borohydride], DIBAL-H (diisobutylaluminum hydride) or the like.

In reductive amination, in addition to reduction using the above hydride reducing agent, reduction can be also performed by a hydrogenation reaction in the presence of a catalyst. As the catalyst, ruthenium, rhodium, palladium, platinum, or nickel can be used. When the hydrogenation reaction is performed in the presence of a catalyst, since hydride is generated in a reaction system, the reaction condition is also included in the above "hydride reducing agent."

Alternatively, reductive amination using sodium can be also performed.

As a salt of the present compound, a pharmaceutically acceptable salt is preferable. Example of the pharmaceutically acceptable salt includes the following salts.

Example of a basic salt includes alkali metal salts such as sodium salt and potassium salt; alkaline earth metal salts such as calcium salt and magnesium salt; ammonium salt; aliphatic amine salts such as trimethylamine salt, triethylamine salt, dicyclohexylamine salt, ethanolamine salt, diethanolamine salt, triethanolamine salt, procaine salt, meglumine salt, diethanolamine salt and ethylenediamine salt; aralkylamine salts such as N,N-dibenzylethylenediamine salt and benethamine salt; heterocyclic aromatic amine salts such as pyridine salt, picoline salt, quinoline salt, and isoquinoline salt; quaternary ammonium salts such as tetramethylammonium salt, tetraethylammonium salt, benzyltrimethylammonium salt, benzyltriethylammonium salt, benzyltributylammonium salt, methyltrioctylammonium salt, and tetrabutylammonium salt; basic amino acid salts such as arginine salt, and lysine salt or the like.

Example of an acidic salt includes inorganic acid salts such as hydrochloride, sulfate, nitrate, phosphate, carbonate, hydrogencarbonate, and perchlorate; organic acid salts such as acetate, propionate, lactate, maleate, fumarate, tartrate, malate, citrate, and ascorbate; sulfonates such as methanesulfonate, isethionate, benzenesulfonate, and p-toluenesulfonate; acidic amino acid salts such as aspartate and glutamate or the like.

Solvate means a solvate of the present compound and a pharmaceutically acceptable salt thereof, and example includes alcohol(e.g., ethanol) solvate, hydrate or the like. Example of hydrate includes monohydrate, dihydrate or the like.

The compound (IV) can be synthesized, for example, by the following method.

[Formual 22]

(wherein R¹ and R² are as defined above; as the compound represented by the formula (I) and 5-hydroxy-2-adamantanone, the known compounds may be used, or compounds derived from the known compounds by the conventional method may be used)

(First Step)

The first step is a step of reacting the compound represented by the formula (I) and 5-hydroxy-2-adamantanone in the presence of a reducing agent.

In the reaction, example of a solvent includes N-dimethylformamide, dimethyl sulfoxide, aromatic hydrocarbons (e.g. toluene, benzene, and xylene), saturated hydrocarbons (e.g. cyclohexane and hexane), halogenated hydrocarbons (e.g. dichloromethane, chloroform, and 1,2-dichloroethane), ethers (e.g. tetrahydrofuran, diethyl ether, dioxane, and 1,2-dimethoxyethane), esters (e.g. methyl acetate and ethyl acetate), ketones (e.g. acetone and methyl ethyl ketone), nitriles (e.g. acetonitrile), alcohols (e.g. methanol, ethanol, isopropanol, and tert-butanol), water, a mixed solvent thereof or the like. Preferable is halogenated hydrocarbons. (e.g. dichloromethane, chloroform, and 1,2-dichloroethane), nitriles (e.g. acetonitrile), ethers (e.g. tetrahydrofuran, diethyl ether, dioxane, and 1,2-dimethoxyethane), alcohols (e.g. methanol, ethanol, isopropanol, and tert-butanol), water or the like.

Preferable is N,N-dimethylformamide, dimethyl sulfoxide, xylene, dichloromethane, chloroform, 1,2-dichloroethane, diethyl ether, dioxane, 1,2-dimethoxyethane, acetonitrile, methanol, ethanol, isopropanol, tert-butanol, toluene, tetrahydrofuran or water, but not limited thereto.

Further preferable is dichloromethane, methanol, or ethanol.

A use amount of the solvent is not particularly limited, but such an arbitrary amount that can form solution or slurry to react can be used. For example, letting a weight of 5-hydroxy-2-adamantanone to be v (g), a minimum amount of the solvent is about 1 v (ml), preferably about 2 v (ml), and more preferably about 3 v (ml). A maximum amount is not particularly limited, but in view of a production efficacy, it is about 20 v (ml), preferably about 15 v (ml), and more preferably about 10 v (ml). To the above prepared solution may be added the compound (I) and an acid.

A use amount of the compound (I) may be directly added to the reaction solution, or may be added after the compound is dissolved in a solvent. The amount used is 1 to 1.5 equivalents relative to that of 5-hydroxy-2-adamantanone.

The acid can be used at 1 to 5 equivalents, preferably 1 to 2 equivalents relative to 5-hydroxy-2-adamantanone. As the acid, acetic acid, formic acid, citric acid, paratoluenesulfonic acid, methanesulfonic acid, trifluoroacetic acid, phosphoric acid, hydrochloric acid or sulfuric acid can be used. In the step, the reaction proceeds without using acid, but preferably with using acid. As acid, acetic acid is preferable.

The reaction solution may be stirred usually at about 0 to 50° C., preferably at about 20 to 40° C. usually for 5 minutes to 5 hours, preferably for 10 minutes to 2 hours to form an imine form, but not limited thereto.

The above prepared reaction solution is cooled to about −20 to 10° C., preferably about −10 to 5° C., but not limited, and a reducing agent is slowly added thereto. Example of the reducing agent includes sodium triacetoxyhydroborate, sodium borohydride, lithium tetrahydroborate, pyridine borane complex, tetrahydrofuran borane complex, 2-picoline borane complex, dimethyl sulfide-borane complex, sodium, sodium cyanoborohydride, lithium triethylborohydride, lithium aluminum hydride, Red-Al [sodium bis(2-methoxyethoxy)aluminum hydride], L-Selectride [lithium tri(sec-butyl)borohydride], K-Selectride [potassium tri(sec-butyl)borohydride], DIBAL-H (diisobutylaluminum hydride) or the like can be used. Preferable is sodium triacetoxyhydroborate, sodium borohydride, lithium tetrahydroborate, pyridine borane complex, tetrahydrofuran borane complex, 2-picoline borane complex, sodium, lithium aluminum hydride or Red-Al. Preferable is sodium borohydride. The amount used is 0.5 to 15 equivalents, preferably 1 to 10 equivalents, but not limited thereto.

The reaction solution may be stirred at about 20 to 40° C., preferably about 20 to 30° C. usually for 10 minutes to 36 hours, preferably 30 minutes to 24 hours, but not limited thereto.

(Second Step)

The second step is a step of obtaining an anti isomer by crystallization purification from a diastereomer mixture.

A solvent used in crystallization is not particularly limited, and after the mixture is dissolved in a solubilizing solvent, a poor solvent can be added to precipitate a crystal. Example of the solubilizing solvent includes esters (e.g. methyl acetate and ethyl acetate), alcohols (e.g.: methanol, ethanol, isopropanol, and tert-butanol), ketones (e.g. acetone and methyl ethyl ketone), ethers (e.g. tetrahydrofuran, diethyl ether, dioxane, and 1,2-dimethoxyethane), aromatic hydrocarbons (e.g. toluene, benzene, and xylene), halogenated hydrocarbons (e.g. dichloromethane, chloroform, and 1,2-dichloroethane) or the like.

As the poor solvent, for example, saturated hydrocarbons (e.g. cyclohexane and hexane), ethers (e.g. tetrahydrofuran, diethyl ether, dioxane, and 1,2-dimethoxyethane), aromatic hydrocarbons (e.g. toluene, benzene, and xylene), water or the like can be used. A volume ratio of the solubilizing solvent and the poor solvent, letting a weight of 5-hydroxy-2-adamantanone to be v (g), is not particularly limited, but an amount of the solubilizing solvent is about 2 v (ml) or less, preferably about 1.5 v (ml), and more preferably about 1 v (ml), and an amount of the poor solvent is about 20 v (ml) or less, preferably about 15 v (ml), and more preferably about 10 v (ml). When crystallization can be performed only with the solubilizing solvent, the poor solvent may not be used. In the crystallization, stirring may be performed at −20 to 40° C., and preferably about 0 to 30° C., but not limited thereto.

The resulting crystal can be obtained by filtration or the like. In this case, since a syn isomer is dissolved in the filtrate, the purification effect by crystallization is obtained.

An X ray diffraction pattern of a crystal of the compound represented by the formula (III) produced in the second step can be obtained by powder X ray diffraction.

Since the crystal is stable, is easy to handle in performing the aforementioned production step, or producing a pharmaceutical composition containing a diastereomer represented by the formula (VI) as an active ingredient, and is of high purity, it is a crystal useful for producing a pharmaceutical composition.

For the crystal of the compound represented by the formula (III), an X ray diffraction pattern will be shown in Example 2 below (X ray diffraction measuring condition: tube CuKα ray, tube voltage 40 kV, tube current 40 mA, d sin θ=nλ (n is integer, d is spacing (unit: angstrom), and θ is diffraction angle (unit: degree))).

These crystals are characterized by each diffraction angle or a value of spacing.

(Third Step)

The third step is a step of subjecting the compound represented by the formula (III) to debenzylation to produce a compound represented by the formula (IV).

As a solvent, the solvents described in the first step can be used. Preferable is ethers (e.g. tetrahydrofuran, diethyl ether, dioxane, and 1,2-dimethoxyethane) or alcohols (e.g. methanol, ethanol, isopropanol, and tert-butanol). An amount used of the solvent is not particularly limited, and such an arbitrary amount that can form a reactive solution or slurry can be used. For example, letting a weight of the compound represented by the formula (III) to be v (g), a minimum amount of the solvent is about 1 v (ml), preferably about 2 v (ml), and more preferably about 3 v (ml). A maximum amount is not particularly limited, but in view of production efficacy, it is about 30 v (ml), preferably about 25 v (ml), and more preferably about 20 v (ml). To the above prepared solution is added a heterogeneous catalyst, and reduction can be performed in the presence of hydrogen gas.

As the heterogeneous catalyst, for example, a palladium/carbon catalyst, a platinum/carbon catalyst or the like can be used. An amount used is not particularly limited, but the catalyst can be used at 0.001 to 1 equivalent, and preferably 0.1 to 1 equivalent.

The reaction solution may be stirred at about 0 to 80° C., preferably about 20 to 40° C. usually for 1 hour to 36 hours, preferably for 2 hours to 24 hours, but not limited thereto.

The step may be performed under the hydrogen gas atmosphere at a normal pressure, or may be performed under the pressurized atmosphere.

As a solvent, the solvents described in the first step can be used.

When $R^5$ is —C(=O)— and X is a hydroxy group, a condensing agent and a base can be used in the step. As the condensing agent, for example, 1,1-carbonyldiimidazole, dicyclohexylcarbodiimide, water-soluble carbodiimide (1-ethyl-3-(3'-dimethylaminopropyl)carbodiimide) or the like can be used. Example of the base includes metal hydrides (e.g. sodium hydride), metal hydroxides (e.g. sodium hydroxide, potassium hydroxide, lithium hydroxide, and barium hydroxide), metal carbonates (e.g. sodium carbonate, calcium carbonate, and cesium carbonate), metal alkoxides (e.g. sodium methoxide, sodium ethoxide, and potassium tert-butoxide), sodium hydrogen carbonate, metal sodium, organic amines (e.g. triethylamine, diisopropylethylamine, DBU, and 2,6-lutidine) or the like.

When $R^5$ is —C(=O)— and X is halogen, the aforementioned bases can be used in the step.

When $R^3$ is —C(=O)—, $R^4$ is optionally substituted alkylene, $R^5$ is a single bond, and X is a leaving group derived from halogen or a hydroxy group, the aforementioned bases can be used in the step.

The reaction condition is not particularly limited, but the reaction solution may be stirred at about −20 to 100° C., preferably at about −10 to 80° C. usually for 1 hour to 36 hours, preferably for 1 hour to 24 hours, but not limited thereto.

The above obtained compound (VI) is useful as an 11β-hydroxysteroid dehydrogenase inhibitor, a Dipeptidyl Peptidase IV (DPP IV) inhibitor, a Jak3 inhibitor or the like.

The following Examples further illustrate the present invention, but the present invention is not limited thereto.

[Formual 23]

(IV)

Fourth step
A-R³—R⁴—R⁵—X
(V)

(VI)

(Fourth Step)

The fourth step is a step of reacting the compound represented by the formula (IV) and the compound represented by the formula (V) to produce a compound represented by the formula (VI).

Example 1

When the formula (I):

[Formula 24]

(I)

is the formula (VII):

[Formula 25]

(VII)

results of reductive amination of 5-hydroxy-2-adamantanone and a compound represented by the formula (VII) are shown in Table 1.

TABLE 1

| Experimental No. | R¹ | R² | Reducing agent (eq.) | Acetic acid | Solvent | Temperature (° C.) | Before purification (NMR ratio) Anti:Syn | After purification (NMR ratio) Anti:Syn |
|---|---|---|---|---|---|---|---|---|
| 1 | H | H | NaBH(OAc)₃ (1.1 eq.) | 1.3 eq. | CH₂Cl₂ | 0 → r.t. | 1.7:1 | — |
| 2 | H | H | NaBH₄ (1.1 eq.) | 1.3 eq. | CH₂Cl₂ | 0 → r.t. | 3.7:1 | 20:1 |
| 3 | H | H | NaBH₄ (1.1 eq.) | 2.1 eq. | CH₂Cl₂ | 0 → r.t. | 3.6:1 | — |
| 4 | H | H | NaBH₄ (0.18 eq.) | 1.3 eq. | CH₂Cl₂ | 0 → r.t. | 5.5:1 | — |
| 5 | H | H | NaBH₄ (1.1 eq.) | 1.3 eq. | MeOH | 0 → r.t. | 4:1 | — |
| 6 | H | H | NaBH₄ (1.1 eq.) | 1.3 eq. | CH₂Cl₂ | 0 | 4:1 | — |
| 7 | H | H | NaBH₄ (1.1 eq.) | 1.3 eq. | CH₂Cl₂ | r.t. | 4:1 | — |
| 8 | H | H | NaBH₄ (1.1 eq.) | 1.3 eq. | CH₂Cl₂ | 50 | 1.8:1 | — |
| 9 | H | H | NaBH₄ (1.1 eq.) | 1.3 eq. | CH₂Cl₂ | −30 → 0 | 2.5:1 | — |
| 10 | H | H | LiBH₄ (1.1 eq.) | 1.3 eq. | CH₂Cl₂ - THF | 0 → r.t. | 2.5:1 | — |
| 11 | H | H | BH₃-Pyridine (1.1 eq.) | 1.3 eq. | MeOH | 0 → r.t. | 1.7:1 | — |
| 12 | H | H | 2-Picoline-Borane(1.1 eq.) | 1.1 eq. | MeOH | r.t. | 2:1 | — |
| 13 | H | H | Na(10 eq.) | 1.3 eq. | THF-IPA | r.t. | 1.7:1 | — |
| 14 | H | H | NaBH₄ (1.1 eq.) | 0 eq. | CH₂Cl₂ | 0 → r.t. | 2:1 | — |
| 15 | OMe | H | NaBH₄ (1.1 eq.) | 1.3 eq. | CH₂Cl₂ | 0 → r.t. | 2.2:1 | 45:1 |
| 16 | F | H | NaBH₄ (1.1 eq.) | 1.3 eq. | CH₂Cl₂ | 0 → r.t. | 4:1 | 13:1 |
| 17 | Cl | H | NaBH₄ (1.1 eq.) | 1.3 eq. | CH₂Cl₂ | 0 → r.t. | 3:1 | 14:1 |
| 18 | Me | H | NaBH₄ (1.1 eq.) | 1.3 eq. | CH₂Cl₂ | 0 → r.t. | 5:1 | 50:1 |

(wherein r.t. means room temperature)

Example 2

[Formual 26]

(Experimental No. 2)

5-Hydroxy-2-adamantanone (9.98 g, 60 mmol) was dissolved in dichloromethane (150 ml), a compound I-1 (7.21 ml, 66 mmol) and acetic acid (4.46 ml, 78 mmol) were added thereto, the mixture was stirred at room temperature for 1 hour, and then sodium borohydride (2.50 g, 66 mmol) was slowly added thereto. The mixture was stirred at room temperature for 6 hours, and allowed to stand at room temperature overnight. The reaction solution was ice-cooled, water (30 ml) was added thereto, the mixture was stirred, and then 2M hydrochloric acid (70 ml) was added thereto. The aqueous layer was washed with chloroform (20 ml), and the organic layer was extracted with 2M hydrochloric acid (10 ml) and water (40 ml). The aqueous layers were combined, 2M aqueous sodium hydroxide solution (70 ml) was added to adjust to pH=8, and the combined aqueous layer was extracted with chloroform (100 ml). The aqueous layer was extracted again with chloroform (50 ml), and the organic layer was washed with saturated brine (50 ml). Organic layers were combined and dried with sodium sulfate, and the organic solvent was evaporated under reduced pressure to obtain a solid (11.4 g, crude yield=73.8%). This solid was a mixture (II-1) in which an anti isomer and a syn isomer were present at a ratio of 3.7:1, by NMR analysis (300 MHz).

This solid was dissolved in warm ethyl acetate (10 ml), then hexane (100 ml) was added thereto, and then the mixture was stirred for 15 minutes and stirred for 1 hour under ice-cooling. The resulting crystal was filtered to obtain a crystal (6.24 g, crude yield=40.4%). This crystal was a mixture in which an anti isomer [compound (III-1)] and a syn isomer were present at a ratio of 20:1, by NMR analysis (300 MHz), and the purification effect by crystallization was identified.

Compound (III-1) ¹H NMR (300 MHz, CDCl₃): d 1.34-2.09 (m, 13H), 2.79 (s, 1H), 3.78 (s, 2H), 7.24-7.36 (m, 5H). m.p.: 106° C.

Figure 1:
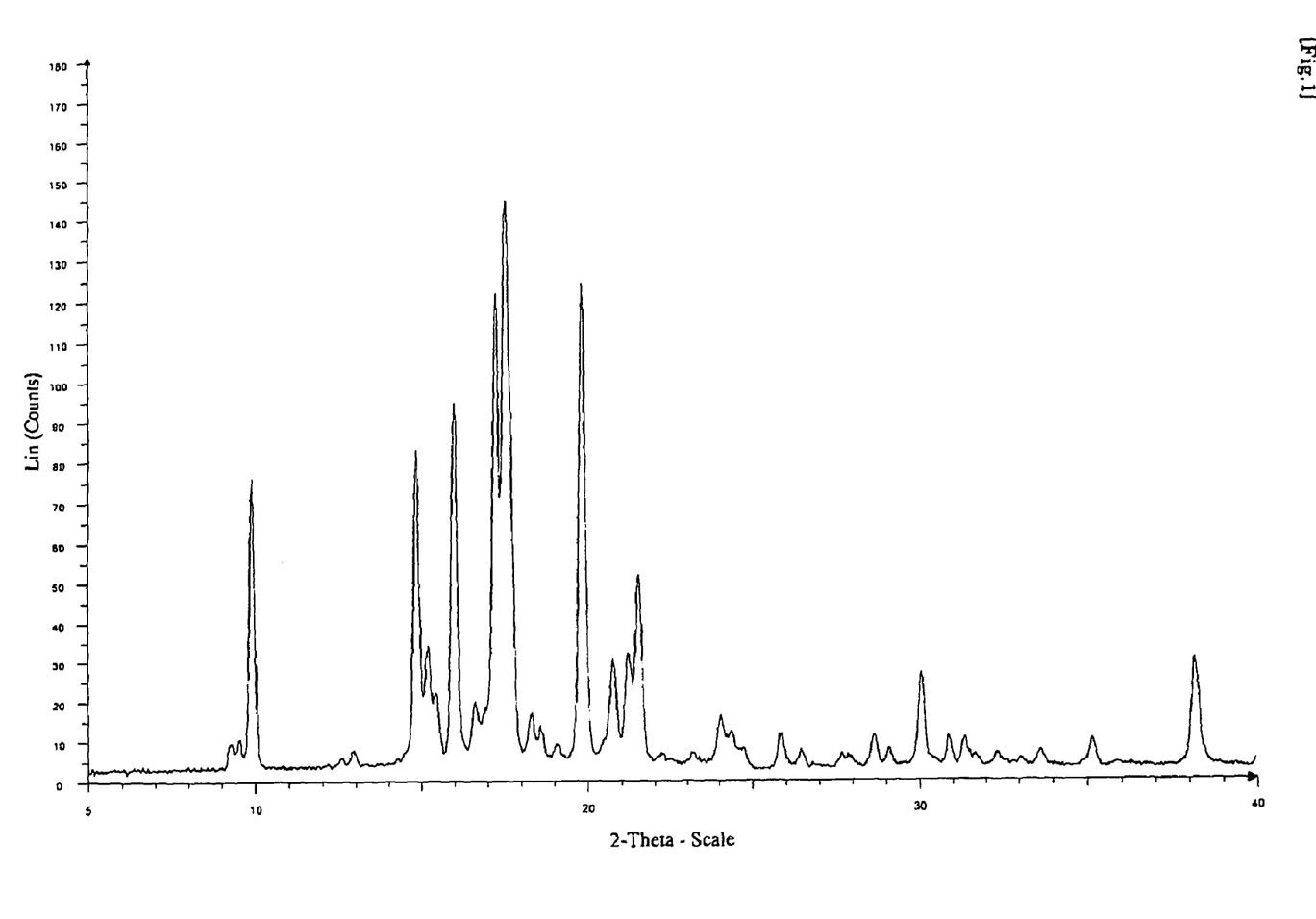
FIG. 1 shows a powder X ray diffraction pattern of the crystal of the compound (III-1) obtained in Example 2, and peak values thereof. An ordinate indicates intensity, and an abscissa indicates a diffraction angle (2θ, unit: degree).

Results of powder X ray diffraction are shown in Table 2 and FIG. 1.

TABLE 2

| Angle 2-Theta ° | d value Angstrom | Intensity % % |
|---|---|---|
| 9.2 | 9.56 | 6.4 |
| 9.5 | 9.30 | 7.2 |
| 9.9 | 8.95 | 52.5 |
| 12.5 | 7.05 | 4.0 |
| 12.9 | 6.85 | 5.5 |
| 14.8 | 5.97 | 57.2 |
| 15.2 | 5.83 | 23.5 |
| 15.4 | 5.75 | 15.3 |
| 16.0 | 5.54 | 65.5 |
| 16.6 | 5.33 | 13.7 |
| 17.2 | 5.14 | 84.3 |
| 17.5 | 5.05 | 100.0 |
| 18.3 | 4.84 | 11.7 |
| 18.6 | 4.78 | 9.5 |
| 19.1 | 4.65 | 6.3 |
| 19.8 | 4.47 | 86.0 |

TABLE 2-continued

| Angle 2-Theta ° | d value Angstrom | Intensity % |
|---|---|---|
| 20.7 | 4.28 | 21.0 |
| 21.2 | 4.19 | 22.0 |
| 21.5 | 4.13 | 35.6 |
| 22.2 | 4.00 | 4.5 |
| 23.2 | 3.84 | 4.7 |
| 24.0 | 3.70 | 11.1 |
| 24.4 | 3.65 | 8.3 |
| 24.7 | 3.60 | 5.7 |
| 25.9 | 3.44 | 7.8 |
| 26.5 | 3.36 | 5.1 |
| 27.7 | 3.22 | 4.6 |
| 28.6 | 3.11 | 7.7 |
| 29.1 | 3.07 | 5.5 |
| 30.1 | 2.97 | 18.4 |
| 30.9 | 2.89 | 7.5 |
| 31.4 | 2.85 | 7.1 |
| 32.4 | 2.76 | 4.7 |
| 33.6 | 2.66 | 5.0 |
| 35.2 | 2.55 | 7.0 |

Diffraction angle of main peaks: 2θ=9.9, 14.8, 16.0, 17.2, 17.5, and 19.8 degree Example 3

[Formula 27]

A compound III-1 (150 mg) was dissolved in tetrahydrofuran (3 ml), 10% palladium carbon (30 mg) was added thereto, and hydrogen gas was introduced therein for 2.5 hours. After the catalyst was filtered, the filtrate was evaporated under reduced pressure to obtain the residue of a compound IV (100 mg, crude yield=102.6%).

Compound (IV) $^1$H NMR (300 MHz, d$_6$-DMSO): d 1.17-1.95 (m, 11H), 2.50 (m, 2H), 2.84 (brs, 1H).

$^{13}$C NMR (75.4 MHz, CDCl$_3$): d 29.3 (2C), 30.0 (1C), 36.8 (2C), 44.8 (2C), 45.6 (1C), 54.3 (1C), 67.5 (1C).

Example 4

[Formual 28]

(Experimental No. 15)

5-Hydroxy-2-adamantanone (0.99 g, 6 mmol) was dissolved in dichloromethane (15 ml), a compound (I-2) (content 98%) (0.88 ml, 6.6 mmol) and acetic acid (0.45 ml, 7.8 mmol) were added thereto, the mixture was stirred at room temperature for 20 minutes, sodium borohydride (0.25 g, 6.6 mmol) was then added thereto under ice-cooling, and the mixture was stirred at room temperature overnight. The reaction solution was ice-cooled, 2M hydrochloric acid (8 ml) and water (15 ml) were added thereto, and the mixture was stirred for a while. The aqueous layer was washed with chloroform (15 ml and 10 ml), and the organic layer was extracted with water (15 ml). The aqueous layers were combined, 2M aqueous sodium hydroxide solution (9 ml) was added to adjust to pH=8 to 9, and the combined aqueous layer was extracted with chloroform (15 ml). The aqueous layer was extracted again with chloroform (10 ml), and the organic layer was washed with a saturated brine (15 ml). The organic layers were combined and then dried with sodium sulfate, and the organic solvent was evaporated under reduced pressure to obtain a colorless oil (1.54 g, crude yield=89.3%). This oil was a mixture (II-2) in which an anti isomer and a syn isomer were present at a ratio of 2.2:1, by NMR analysis (300 MHz).

This oil was dissolved in warm ethyl acetate (2 ml), then heptane (30 ml) was added thereto, and then the mixture was stirred, and the resulting crystal was filtered to obtain crystal (0.36 g, crude yield=20.8%). This crystal was a mixture in which an anti isomer [compound (III-2)] and a syn isomer were present at a ratio of 45:1, by NMR analysis (300 MHz), and the purification effect by crystallization was identified.

Compound (III-2) $^1$H NMR (300 MHz, CDCl$_3$): d 1.33-2.07 (m, 13H), 2.76 (s, 1H), 3.70 (s, 2H), 3.80 (s, 3H), 6.86 (dd, J=2.1 Hz, 6.6 Hz, 2H), 7.26 (d, J=8.4 Hz, 2H).

m.p.: 75° C.

Example 5

[Formula 29]

(Experimental No. 16)

5-Hydroxy-2-adamantanone (0.99 g, 6 mmol) was dissolved in dichloromethane (15 ml), a compound (I-3) (content 97%) (0.78 ml, 6.6 mmol) and acetic acid (0.45 ml, 7.8 mmol) were added thereto, the mixture was stirred at room temperature for 15 minutes, sodium borohydride (0.25 g, 6.6 mmol) was then added thereto under ice-cooling, and the mixture was stirred at room temperature for 2 days. The reaction solution was ice-cooled, 2M hydrochloric acid (8 ml) and water (15 ml) were added thereto, and the mixture was stirred for a while. The aqueous layer was washed with chloroform (15 ml and 10 ml), and the organic layer was extracted with water (15 ml). The aqueous layers were combined, 2M aqueous sodium hydroxide solution (9 ml) was added to adjust to pH=8 to 9, and the combined aqueous layer was extracted with chloroform (15 ml). The aqueous layer was extracted again with chloroform (10 ml), and the organic layer was washed with a saturated brine (15 ml). The organic layers were combined and then dried with sodium sulfate, and the organic solvent was evaporated under reduced pressure to obtain a colorless oil (1.51 g, crude yield=91.4%). This oil was a mixture (II-3) in which an anti isomer and a syn isomer were present at a ratio of about 4:1, by NMR analysis (300 MHz).

This oil was dissolved in warm ethyl acetate (2 ml), then heptane (30 ml) was added thereto, and then the mixture was stirred, and the resulting crystal was then filtered to obtain a crystal (0.32 g, crude yield=19.2%). This crystal was a mixture in which an anti isomer [compound (III-3)] and a syn isomer were present at a ratio of 13:1, by NMR analysis (300 MHz), and the purification effect by crystallization was identified.

Compound (III-3) $^1$H NMR (300 MHz, CDCl$_3$): d 1.34-2.06 (m, 13H), 2.76 (s, 1H), 3.73 (s, 2H), 6.97-7.03 (m, 2H), 7.65-7.33 (m, 2H).

m.p.: 79° C.

Example 6

[Formula 30]

(Experimental No. 17)

5-Hydroxy-2-adamantanone (0.99 g, 6 mmol) was dissolved in dichloromethane (15 ml), a compound (I-4) (content 98%) (0.82 ml, 6.6 mmol) and acetic acid (0.45 ml, 7.8 mmol) were added thereto, the mixture was stirred at room temperature for 20 minutes, sodium borohydride (0.25 g, 6.6 mmol) was then added under ice-cooling, and the mixture was stirred at room temperature for 2 days. The reaction solution was ice-cooled, 2M hydrochloric acid (8 ml) and water (15 ml) were added thereto, and the mixture was stirred for a while. The aqueous layer was washed with chloroform (15 ml and 10 ml), and the organic layer was extracted with water (15 ml). The aqueous layers were combined, 2M aqueous sodium hydroxide solution (9 ml) was added to adjust to pH=8 to 9, and the combined aqueous layer was extracted with chloroform (15 ml). The aqueous layer was extracted again with chloroform (10 ml), and the organic layer was washed with saturated brine (15 ml). The organic layers were combined and then dried with sodium sulfate, and the organic solvent was evaporated under reduced pressure to obtain a colorless oil (1.35 g, crude yield=77.1%). This oil was a mixture (II-4) in which an objective anti isomer and a syn isomer were present at a ratio of about 3:1, by NMR analysis (300 MHz).

This oil was dissolved in warm ethyl acetate (2 ml), then heptane (30 ml) was added thereto, and then the mixture was stirred, and the resulting crystal was then filtered to obtain a crystal (0.31 g, crude yield=17.7%). This crystal was a mixture in which an anti isomer [compound (III-4)] and a syn isomer were present at a ratio of about 14:1, by NMR analysis (300 MHz), and the purification effect by crystallization was identified.

Compound (III-4) $^1$H NMR (300 MHz, CDCl$_3$): d 1.34-2.05 (m, 13H), 2.75 (s, 1H), 3.74 (s, 2H), 7.27-7.29 (m, 4H). m.p.: 91° C.

Example 7

[Formual 31]

(Experimental No. 18)

5-Hydroxy-2-adamantanone (0.99 g, 6 mmol) was dissolved in dichloromethane (15 ml), a compound (I-5) (content 97%) (0.87 ml, 6.6 mmol) and acetic acid (0.45 ml, 7.8 mmol) were added thereto, the mixture was stirred at room temperature for 30 minutes, sodium borohydride (0.25 g, 6.6 mmol) was then added under ice-cooling, and the mixture was stirred at room temperature overnight. The reaction solution was ice-cooled, 2M hydrochloric acid (8 ml) and water (15 ml) were added thereto, and the mixture was stirred for a while. The aqueous layer was washed with chloroform (15 ml and 10 ml), and the organic layer was extracted with water (15 ml). The aqueous layers were combined, 2M aqueous sodium hydroxide solution (9 ml) was added to adjust to pH=8 to 9, and the combined aqueous layer was extracted with chloroform (15 ml). The aqueous layer was extracted again with chloroform (10 ml), and the organic layer was washed with a saturated brine (15 ml). The organic layers were combined and then dried with sodium sulfate, and the organic solvent was evaporated under reduced pressure to obtain a colorless oil (1.15 g, crude yield=70.6%). This oil was a mixture (II-5) in which an objective anti isomer and a syn isomer were present at a ratio of about 5:1, by NMR analysis (300 MHz).

This oil was dissolved in warm ethyl acetate (2 ml), then heptane (20 ml) was added thereto, and then the mixture was stirred, and the resulting crystal was then filtered to obtain a crystal (0.53 g, crude yield=32.7%). This crystal was a mixture in which an anti isomer [compound III-5]] and a syn isomer were present at a ratio of about 50:1, by NMR analysis (300 MHz), and the purification effect by crystallization was identified.

Compound (III-5) $^1$H NMR (300 MHz, CDCl$_3$): d 1.32-2.07 (m, 13H), 2.33 (s, 3H), 2.77 (s, 1H), 3.72 (s, 2H), 7.13 (d, J=8.1 Hz, 2H), 7.23 (d, J=8.1 Hz, 2H). m.p.=103° C.

Example 8

[Formual 32]

To a dimethylformamide solution (DMF) (5 ml) of a compound V-1 (150 mg) were added monohydroxy-2-adamantamine (140 mg), 1-hydroxybenzotriazole (HOBT) (31 mg), 1-(3-dimethylaminopropyl)-3-ethylcarbodiimide hydrochloride (WSC) (174 mg), and triethylamine (TEA) (180 μl) under the nitrogen atmosphere, and the mixture was stirred at room temperature for 14 hours. After completion of the reaction, 2N hydrochloric acid (30 ml) was added thereto followed by extraction with ethyl acetate. The organic layer was washed successively with aqueous saturated sodium hydrogen carbonate solution and saturated brine, and dried with magnesium sulfate. A solvent was evaporated, and the residue was purified by silica gel chromatography to obtain a compound VI-1 (226 mg).

$^1$H NMR: (CDCl$_3$); d 1.06 (d, J=6.6 Hz, 6H), 1.53-2.20 (m, 14H), 3.72 (s, 3H), 3.98 (d, J=6.6 Hz, 2H), 6.25-6.30 (m, 1H), 7.71 (s, 1H).

Reference Example 1

The mother washed liquid at filtration obtained in Example 2 was concentrated under reduced pressure, the solvent was evaporated, thereafter, silica gel chromatography (chloroform:methanol=100:0 to 94:6) was performed, and fraction solutions corresponding to the formula (III-1'):

[Formula 33]

(III-1')

were collected. This solution was concentrated under reduced pressure to obtain an oil, which was allowed to stand at room temperature for a while to obtain a solid (0.98 g) of a compound (III-1').

Compound (III-1') $^1$H NMR (300 MHz, CDCl$_3$): d 1.46-1.71 (m, 9H), 2.06-2.15 (m, 4H), 2.67 (dd, J=2.4 Hz, 2.4 Hz, 1H), 3.77 (s, 2H), 7.24-7.34 (m, 5H).

m.p.: 72° C.

Comparative Example 1

According to the method described in Patent Document 1, 11.0 g (anti isomer: syn isomer=3:1) of a compound (VIII):

[Formula 34]

(VIII)

was produced. AcOEt (11 ml) was added to the resulting compound (VIII) to dissolve it, and hexane (110 ml) was slowly added at room temperature. After the solution became cloudy slight, it was stirred for a while, a small amount of oil was adhered to a wall surface, but precipitation of crystal was not confirmed.

INDUSTRIAL APPLICABILITY

According to the present process, it is possible to produce compounds (III) and (IV) effectively, and the process is useful as industrial process.

The invention claimed is:

1. A compound represented by the formula (II):

(II)

(wherein $R^1$ and $R^2$ are each independently hydrogen, halogen, carboxy, nitro, optionally substituted alkyl, optionally substituted alkoxy, optionally substituted alkylsulfonyl, optionally substituted arylsulfonyl, or optionally substituted sulfamoyl, or $R^1$ and $R^2$, when a binding carbon atom is adjacent, may be taken together with an adjacent carbon atom to form an optionally substituted ring) (with the proviso that, the case where $R^1$ and $R^2$ are hydrogen at the same time is excluded), or a salt thereof.

2. A compound represented by the formula (III):

(III)

(wherein $R^1$ and $R^2$ are each independently hydrogen, halogen, carboxy, nitro, optionally substituted alkyl, optionally substituted alkoxy, optionally substituted alkylsulfonyl, optionally substituted arylsulfonyl, or optionally substituted sulfamoyl, or $R^1$ and $R^2$, when a binding carbon atom is adjacent, may be taken together with an adjacent carbon atom to form an optionally substituted ring) (with the proviso that, the case where $R^1$ and $R^2$ are hydrogen at the same time is excluded), or a salt thereof.

* * * * *